(12) United States Patent
Shirahase et al.

(10) Patent No.: US 6,586,194 B1
(45) Date of Patent: Jul. 1, 2003

(54) METHOD FOR ASSAYING CREATINE KINASE ISOZYME ACTIVITY AND ASSAY REAGENT

(75) Inventors: Yasushi Shirahase, Hyogo (JP); Tadahiro Kajita, Hyogo (JP); Tadashi Hoshino, Tokyo (JP)

(73) Assignee: International Reagents Corporation, Hyogo (JP)

( * ) Notice: Subject to any disclaimer, the term of this patent is extended or adjusted under 35 U.S.C. 154(b) by 0 days.

(21) Appl. No.: 09/665,063

(22) Filed: Sep. 19, 2000

Related U.S. Application Data

(63) Continuation-in-part of application No. PCT/JP00/00195, filed on Jan. 18, 2000.

(30) Foreign Application Priority Data

Jan. 19, 1999 (JP) .......................................... 11/010624

(51) Int. Cl.⁷ ........................ G01N 33/00; G01N 33/53; C12Q 1/66
(52) U.S. Cl. .............................. 435/7.92; 435/5; 435/6; 435/7.21; 435/184; 435/188; 435/188.7; 435/287.1; 435/810; 436/4; 436/6; 436/500; 436/501; 436/514; 436/536; 436/518; 422/50; 422/55; 422/57; 422/58; 422/68.1; 424/1; 424/1.5; 424/8; 424/12; 424/85; 23/230 B
(58) Field of Search ................................ 435/5, 7, 184, 435/188, 810, 287.1, 88.7; 424/8, 12; 23/230 B; 436/500, 501, 4, 6, 514; 422/50, 68.1, 55, 57, 58

(56) References Cited

FOREIGN PATENT DOCUMENTS

WO   WO 97/08551   *   3/1997   ..........   G01N/33/53

OTHER PUBLICATIONS

Wu et al., "Evalauation and comparison of immunoihibition and immunoprecipitation methods for differentiating MB and BB from macro forms of creatine kinase isoenzymes in patients and healthy individuals". Clinical Chemistry. Oct. 1982.*

Valdya et al., "Direct measurement of creatine kinase–MB activity in serum after extraction with a monoclonal antibody specific to the MB isoenzyme." Clinical Chemistry, vol. 32., No. 4., pp. 657–663, 1986.*

Panteghini et al., "A two–tube immunchemical method for determination of CK–MB isoenyzmes in serum evaluated." Clinical Chemistry, vol. 36., No. 3., pp. 550–553, 1990.*

Apple et al., "Clinical and analytical evalauation of two immunoassays for direct measurement of creatine kinase MB with monoclonal anti–CK–MD–antibodies." Clinical Chemistry, vol. 34., No. 11., 1988.*

Chandler et al., "Creatine kinase isoenzymes in human cerebrospinal fluid and brain." Clinical Chemistry, Vo.30., No. 11., 1984, pp. 1804–1806.*

Desjardins., "Characterization of an atypical creatine kinase from human heart tissue, with properties similar to those of mitochondrial creatine kinase." Clinica Chimica Acta, vol. 121, 1982, pp. 67–78.*

* cited by examiner

Primary Examiner—Christopher L. Chin
Assistant Examiner—Lisa V Cook
(74) Attorney, Agent, or Firm—Sughrue Mion, PLLC

(57) ABSTRACT

A method for measuring the activity of creatine kinase MB (CK-MB) isozyme which is accurate, high in specificity, convenient, by inhibiting the activity of a mitochondria localized creatine kinase (mCK) isozyme to avoid the influence of mCK and a measurement reagent therefor.

7 Claims, 2 Drawing Sheets

METHOD FOR ASSAYING CREATINE KINASE ISOZYME ACTIVITY AND ASSAY REAGENT

Figure 1:
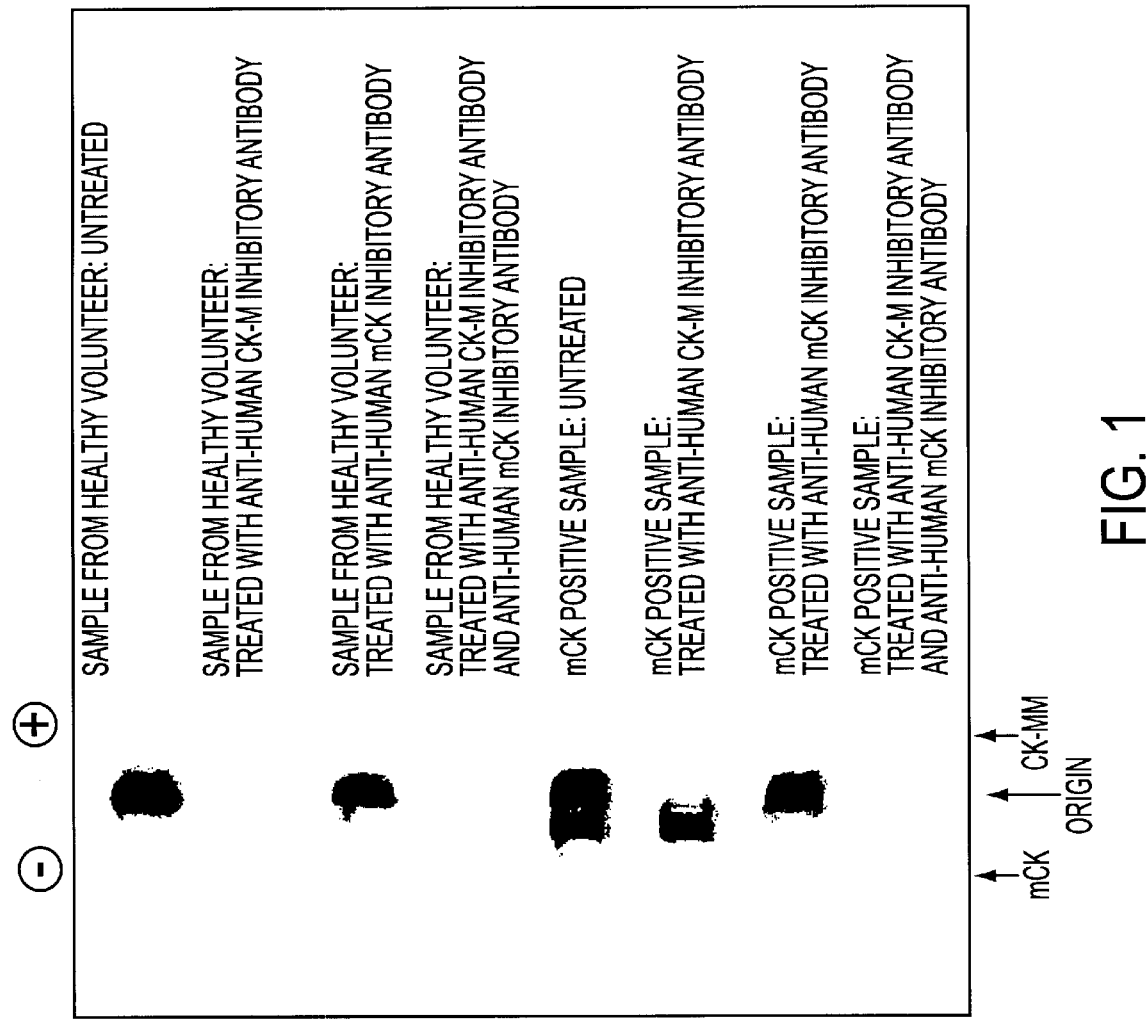

This is a Continuation-in-Part Application of PCT/JP00/00195, filed Jan. 18,2000 benefit of which is requested. In addition, priority is claimed from Japanese Application No. 11/10624 filed Jan. 19, 1999.

TECHNICAL FIELD

The present invention relates to a method for assaying the activity of creatine kinase (CK) isozyme and to an assay reagent therefor. More particularly, the present invention relates to a method for assaying the activity of creatine kinase MB isozyme (CK-MB) and/or the activity of creatine kinase isozyme localized in mitochondria (mCK) and to an assay reagent therefor.

BACKGROUND ART

Human CK includes four proteins whose genes are different. They consist of two kinds of proteins originated from cytoplasms [muscle-type (M-type) and brain-type (B-type) depending on where they are localized] and two kinds of proteins originated from mitochondria, sarcomeric CK (smCK) and ubiquitous CK (umCK). smCK exists in heart muscles and skeletal muscles while umCK is present in small intestines, brains, and stocmachs. The CK isozymes originated from cytoplasms consist of dimers and are classified into 3 types, CK-MM, CK-MB, and CK-BB [Y. Takagi, R. Uzawa, and K. Gomi: Rinsho Kensa (*Journal of Medical Technology*), Vol. 32, 1309–1315 (1988)]. mCK, which exists in the form of octamer in tissues, is converted with time to dimers in blood. Hereinafter, mCK is meant to include smCK and/or umCK.

The mobilities of the isozymes in electrophoresis are arranged in the order of mCK (octamer), and mCK (dimer)= CK-MM, CK-MB, CK-BB from the cathode. smCK and umCK have equivalent mobilities. Since mCK (dimer) shows the same mobility as that of CK-MM, mCK (dimer) in stored blood is measured as CK-MM by electrophoresis. Besides, there are macro-CKs, which consist of CK and an immunoglobulin connected thereto although they are not classified into isozymes. They can be confirmed from zymograms by mobility, an immune countercurrent method. The properties of the isozymes of CK are shown in Table 1.

TABLE 1

|  | CK-1 | CK-2 | CK-3 | mCK Dimer | Octamer |
|---|---|---|---|---|---|
| Subunit | BB | MB | MM |  |  |
| Molecular weight | 82,000 | 82,000 | 82,000 | 84,000 | 320,000 |
| Tissue | Brain | Cardiac muscle | Skeletal muscle |  |  |
| % Inhibition by anti-CK-M antibody | – | 50–60% | + | – | – |

In clinical tests, determination of total CK or CK-MB has been widely performed. Particularly, CK-MB is important as a marker for myocardial infarction. Determination methods of CK-MB include an EIA method, an immunological inhibition method, an electrophoretic method, etc.

The EIA method can measure only CK-MB with high specificity whereas it requires a special apparatus and is not quick. The electrophoretic method is cumbersome to operate and requires expertness. It is necessary to obtain the ratio of CK-MB by means of a densitometer before results can be obtained so that this method is not quick either. The immunological inhibition method is advantageous in that quick and easy measurement can be performed by means of an automatic analyzer. However, it has a disadvantage that it lacks specificity.

However, currently, early stage diagnosis of acute myocardial infarction (hereinafter, sometimes referred to as AMI for short) is desired, so that an immunological inhibition method has been widely used. This method uses an inhibitory antibody to human CK-M subunit to deactivate the M subunit and determines the activity of the remaining B subunit. Use of the method results in measurement of unintended CK-BB and mCKs (dimer and octamer) as well as CK-MB. Of these, CK-BB, which scarcely exists in blood, may be neglected. In addition, there are not so many diseases which involve exudation of it (release of it from the tissue into blood by the destruction of tissue or the like). However, mCK is contained in the sera of healthy persons in amounts substantially the same as CK-MB in terms of activity [Y. Toyoda, et al.: Seibutsu Butsuri Kagaku (*Japanese Journal of Electrophoresis*), Vol. 42, 175–179 (1998) and T. Hoshino, et al., Seibutsu Butsuri kagaku (*Japanese Journal of Electrophoresis*), Vol. 42, Supplement No. 2, 21 (1998)]. Furthermore, the exudation of mCK occurs in the case of necrosis of cells as in liver diseases, malignant tumors, etc., which confuses the judgment of the results. Recently, it has been reported that the exudation of mCK occurs in enteritis due to rotavirus, infant apnea, etc. [T. Hoshino, et al.; Rinsho Byori (*The Japanese Journal of Clinical Pathology*), 46, Plenary Assembly Issue, 57 (1998) and F. Kanemitsu, et al.; Rinsho Bori (*The Japanese Journal of Clinical Pathology*), 46, Plenary Assembly Issue, 56 (1998)]. In addition, by this measurement method, about half the CK-MB activity is also inhibited and hence the activity is calculated by multiplying the measured value by 2. This doubles the influence of mCK activity. That is, the method of selectively measuring the enzymatic activity of CK isozyme by the conventional immunological inhibition method measures CK-MB activity by using an anti-human CK-M inhibitory antibody and enables convenient and quick measurement. However, this method also measures the activity of mCK simultaneously so that no accurate measurement of CK-MB activity can be expected.

DISCLOSURE OF THE INVENTION

An object of the present invention is to provide a method for measuring the activity of CK-MB which is free of the influence by mCK, accurate, high in specificity, and convenient and which permits automation if desired, by selectively and immunologically eliminating the enzymatic action of mCK. Another object of the present invention is to provide a measurement reagent for use in the measurement method.

As a result of extensive investigation, it has been found that the above objects can be achieved by measuring the activity of CK after treatment of selectively and immunologically eliminating the enzymatic actions of CK-M subunit and mCK, thus completing the present invention.

That is, in one aspect, the present invention relates to a method for measuring the activity of CK-MB isozyme comprising selectively measuring the enzymatic activity of CK isozymes by an immunological inhibition method, wherein after a treatment of selectively and immunologically eliminating the enzymatic actions of CK-M subunit and mCK is performed, the activity of remaining CK is measured.

In another aspect, the present invention relates to the method for measuring the activity of CK-MB isozyme as described above, wherein the treatment of selectively and immunologically eliminating the enzymatic actions of CK-M subunit and mCK is a treatment in which an inhibitory antibody to the CK-M subunit and an inhibitory antibody to the mCK are used.

In still another aspect, the present invention relates to the method for measuring the activity of CK-MB isozyme as described above, wherein the inhibitory antibody to the CK-M subunit and the inhibitory antibody to the mCK are simultaneously acted in one step.

In yet another aspect, the present invention relates to the method for measuring the activity of CK-MB isozyme as described above, wherein the inhibitory antibody to the CK-M subunit and the inhibitory antibody to the mCK are acted in different steps.

In a further aspect, the present invention relates to the method for measuring the activity of CK-MB isozyme, wherein the inhibitory antibody to the CK-M subunit is acted and measurement of the activity of CK is performed and then the inhibitory antibody to the mCK is acted and the measurement is performed again to simultaneously achieve measurement of the activity of mCK.

In a still further aspect, the present invention relates to a method for measuring the activity of mCK comprising measuring the activity of CK, acting an inhibitory antibody to mCK, and again performing the measurement.

In a yet further aspect, the present invention relates to a measurement reagent for measuring CK isozymes, comprising a reagent necessary for a measurement method as described above as a kit or as a single item.

BRIEF DESCRIPTION OF THE ATTACHED DRAWINGS

FIG. 1 is an electrophoretograms of samples from healthy persons and mCK-positive samples treated with anti-human CK-M inhibitory antibody and mCK inhibitory antibody.

Figure 2:
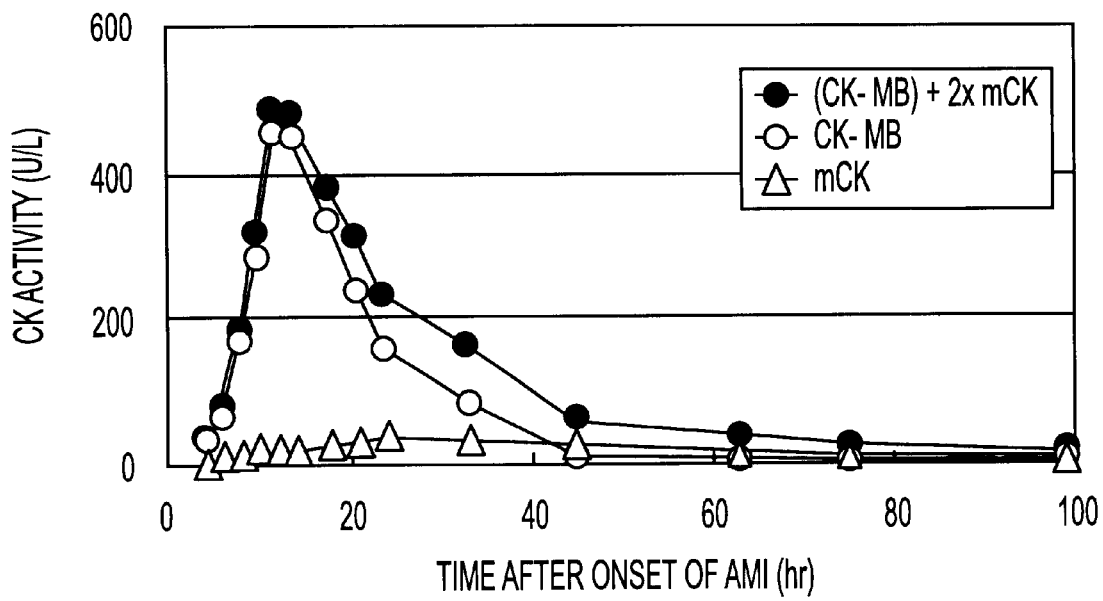

FIG. 2 is a drawing comparing the results of the activity of CK measured by the control method (-●-; CK-MB activity +2×mCK activity) and the activity of CK measured by the measurement method of the present invention (-○-; CK-MB activity, -Δ-; mCK activity) on cases of acute myocardiac infarction (AMI) with prognosis good.

Figure 3:
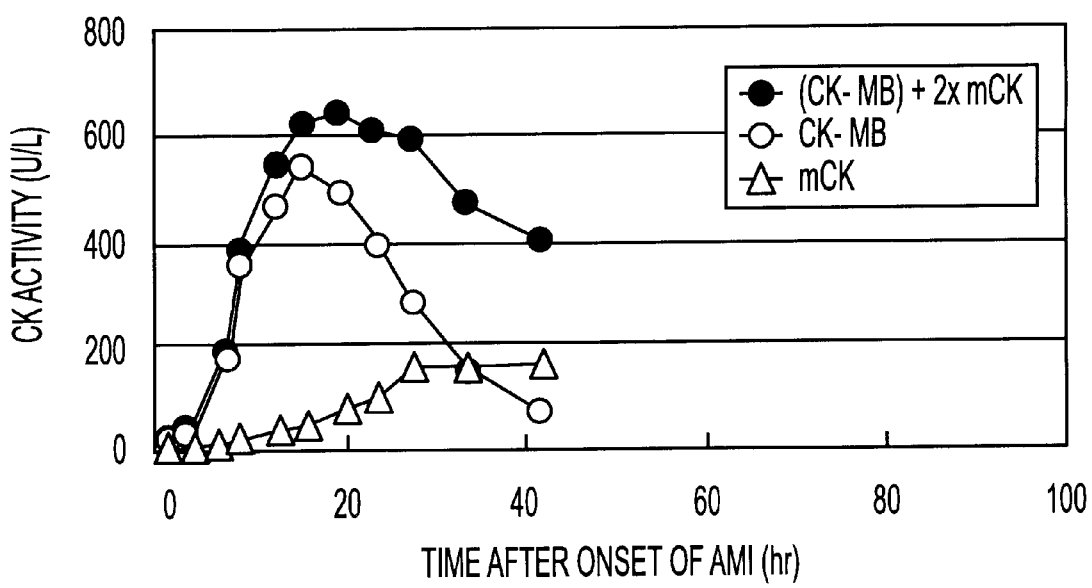

FIG. 3 is a drawing comparing the results of the activity of CK measured by the control method (-●-; CK-MB activity +2×mCK activity) and the activity of CK measured by the measurement method of the present invention (-○-; CK-MB activity, -Δ-; mCK activity) on cases of acute myocardiac infarction (AMI) with bad prognosis.

BEST MODE FOR CARRYING OUT THE INVENTION

The present invention has been completed based on the finding that in a method for measuring the activity of a CK isozyme, use of inhibitory antibodies in combination enables selective assay of the activity of the CK isozyme.

According to a first embodiment of the present invention, the method for assaying the activity of a CK isozyme is one for selectively assaying the enzymatic activity of a CK isozyme by an immunological inhibition method, characterized in that a sample is subjected to a treatment with an inhibitory antibody to human CK-M subunit (anti-human CK-M inhibitory antibody) and an inhibitory antibody to human mCK (anti-human mCK inhibitory antibody) to selectively and immunologically eliminate the enzymatic actions of CK-M subunit and mCK and then the remaining CK activity is measured.

According to a second embodiment of the present invention, the method for assaying the enzymatic activity of a CK isozyme is one for selectively assaying the activity of a CK isozyme by an immunological inhibition method, characterized in that the enzymatic actions of CK-M subunit and mCK are selectively and immunologically eliminated separately and then both CK-MB activity and mCK activity are measured. That is, the method is characterized in that measurement is performed by inhibiting all the activity of CK-MM and about half the activity of CK-MB with anti-human CK-M inhibitory antibody and then anti-human mCK inhibitory antibody is added and a further measurement is performed.

According to a third embodiment of the present invention, the method for assaying the enzymatic activity of a CK isozyme is one for selectively assaying the activity of a CK isozyme by an immunological inhibition method, characterized in that the enzymatic action of mCK is selectively and immunologically eliminated and the activity of mCK is measured. That is, the method is characterized in that the activity of CK is measured, an anti-human mCK inhibitory antibody is added, and then a further measurement is performed.

The basic principle of the present invention utilizes a method for selectively assaying the enzymatic activity of a CK isozyme by an immunological inhibition method. Generally, the assay of the enzymatic activity of CK-MB by this method is carried out as follows. That is, an activity inhibitory antibody specific to human CK-M subunit is used to inhibit the activity of the M subunit in MM and MB of serum CK (for MB, about half the activity is inhibited) and the remaining B subunit activity is doubled, thereby measuring the activity of CK-MB. The measurement of the activity of CK-MB is carried out by an ultraviolet measuring method utilizing an enzyme reaction system using, for example, hexokinase (HK) and glucose-6 phosphate dehydrogenase (G-6-PDH). The assaying method is an initial rate measuring method (chemical formula 2) which measures ATP produced by a leftward reaction in the following reaction scheme (chemical formula 1) as an increase in absorbance at 340 nm of NADPH by a coupling reaction between hexokinase (HK) and G-6-PDH.

Chemical Formula 1

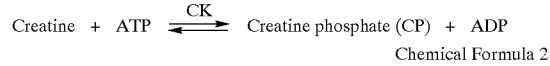

Chemical Formula 2

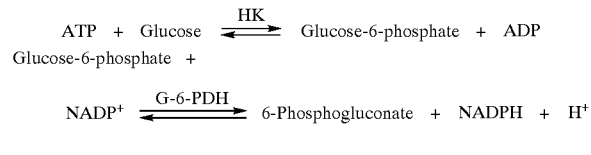

Measurement of the activity of CK-MB with an inhibitory antibody to anti-human CK-M by a conventional method also measures the activity of mCK simultaneously so that no accurate measurement of the activity of CK-MB can be expected. In contrast, in the present invention, measurement of the activity of CK-MB which is practically sufficiently accurate can be performed conveniently and quickly by inhibiting the activity of mCK with an inhibitory antibody to anti-human MCK.

Further, the present invention can assay the activity of CK-MB conveniently and quickly by inhibiting all the activity of CK-MM and about half the activity of CK-MB by using an anti-human CK-M inhibitory antibody, measuring the remaining enzymatic activity of the CK isozyme, adding an anti-human mCK inhibitory antibody, and measuring the still remaining enzymatic activity of CK isozyme. By subtracting the value of the CK-MB activity from the initially measured enzymatic activity of CK isozyme, the activity of mCK can be obtained.

More specifically, where the isozyme of which measurement of activity is intended is CK-MB, the sample is treated with an anti-human CK-M inhibitory antibody and an anti-human mCK inhibitory antibody to inhibit the activity of the M subunit in MM and MB of serum CK and the activity of mCK, the remaining activity of B subunit is measured and then the measured value is doubled to obtain a CK-MB activity. Since substantially no CK-BB is present in blood, this can be ignored.

On the other hand, where the CK isozyme of which measurement of activity is intended includes CK-MB and mCK, first the sample is treated with an anti-human CK-M inhibitory antibody and the activity of CK is measured. Then, the sample is treated with an anti-human mCK inhibitory antibody and the activity of CK which still remains is measured again and the measured value is doubled to obtain a CK-MB activity. By subtracting the activity of CK obtained in the second measurement from the activity of CK obtained in the first measurement, the value of the activity of mCK can be obtained. In this manner, the assaying method of the present invention can give both the activity of mCK and the activity of CK-MB in the same sample simultaneously.

Where only the activity of mCK is the object of measurement, the activity of CK is measured and then the sample is treated with an anti-human mCK inhibitory antibody and the remaining activity of CK is measured again. By subtracting the activity of CK obtained in the second measurement from the activity of CK obtained in the first measurement, the activity of mCK can be obtained.

The inhibitory antibodies used upon the activity inhibition treatment for removing the activity of unnecessary CK isozyme or CK-M subunit may be used separately for treating the sample but they may be used simultaneously for treating the sample. Where the anti-human CK-M inhibitory antibody and anti-human mCK inhibitory antibody are antibodies prepared in different animal species, they may form precipitates, etc. when they are mixed. In such a case, the antibodies may be used after treating one of them with affinity column in which the immunoglobulin of the other animal is immobilized. More preferably, to avoid the risk of the existence of heterophile antibody, it is recommended that they will be separately acted on the sample.

The inhibitory antibodies may be used for the treatment of samples as a reagent prepared independently of an enzyme reagent and/or a substrate solution used for the enzymatic reaction system for the measurement of the activity of CK or as a reagent prepared by addition of them in an enzyme reagent and/or a substrate solution.

The measurement of the activity of CK can be performed by a usual assaying method using as a reagent, for example, CPK Reagent L "KOKUSAI" manufactured by International Reagents Corporation.

The anti-human CK-M inhibitory antibody and anti-human mCK inhibitory antibody used in the assaying method of the present invention can be obtained, for example, by immunizing goat with a human CK-M subunit or a human mCK fraction, collecting and purifying the antibody according to a conventional method [J. Schelegel et al., $J.\ B.\ C.$, Vol. 263, No. 32, pp. 16942–16953 (1988)].

Specifically, the anti-human mCK inhibitory antibody can be prepared as follows. That is, as the antigen human or mammalian mCK is used although it may vary depending on the intended specificity. To increase specificity, it is preferred to use species-specific antigens.

Where it is intended to obtain an antibody having affinity to human mCK specifically and specifically inhibiting the enzymatic activity of human mCK, the antigen can also be prepared by genetic engineering techniques.

As the sensitizing antigen, use is made of one obtained by dissolving or suspending a purified mCK protein molecule or expressed protein according to a partial amino acid sequence prepared by genetic engineering in a suitable buffer such as a phosphate buffer solution (PBS). The antigen liquid may be prepared to a concentration of usually about 50 to about 500 $\mu$g/ml in terms of the antigen substance. In the case of antigen substances which alone are low in antigenicity, such as peptide antigens, it is preferred that they be connected by crosslinking to a suitable carrier protein such as albumin or keyhole limpet hemocyanin before they can be used.

The animals to be immunologically sensitized with the antigen include, for example, mice, rats, horses, goats, rabbits, etc., preferably mice, and more preferably BALB/c mouse. To increase the response by animals to be immunized to the antigen, the above solution may be mixed with an adjuvant before it can be administered. The adjuvant includes Freund's complete adjuvant (FCA), Freund's incomplete adjuvant (FIA), Ribi (MPL), Ribi (TDM), Ribi (MPL+TDM), *Bordetella pertussis* vaccine, muramyl dipeptide (MDP), aluminum adjuvant (ALUM), and combinations thereof. A combination of using FCA for initial immunization and using FIA or Ribi adjuvant for additional immunization is particularly preferably.

The immunization method may be changed appropriately with respect to site of injection, schedule, etc. depending on the type of antigen used and whether or not it is mixed with an adjuvant. For example, where a mouse is used as an animal to be immunized, 0.05 to 1 ml of an adjuvant-mixed antigen liquid (antigen substance: 10 to 200 $\mu$g) is administered by intraperitoneal, subcutaneous, or intramuscular injection, or injection in the (caudal) vein and additional immunization is performed 1 to 4 times every about 4 to 21 days from the initial immunization, followed by a final immunization after about 1 to 4 weeks. Where the above antigen solution is administered without using any adjuvant, intraperitoneal injection may be used with an increased amount of antigen. The antibody dilution titer is examined by collecting blood about 5 to 6 days after the additional immunization. Measurement of antibody dilution titer can be carried out by conventional methods in a manner similar to the antibody titer assay as described hereinbelow. About 3 to 5 days from the final immunization, spleen cells are separated from the immunized animal to obtain antibody-producing cells. Where a polyclonal antibody is utilized, plasma is obtained from the collected blood and the plasma is purified by a purification method for antibodies, known per se, with optionally adjusting the purity thereof.

The antibodies alone or in combination can specifically inhibit the enzymatic activity of mCK in the sample to enable specific measurement of the activity of CK-MB. Furthermore, in the present invention, antiserum per se or purified IgG antibody, further Fab fragment obtained by digesting an antibody with papain can be used.

Samples measured by the present invention are not particularly limited and those used in the art in methods for measuring CK-MB may be used.

In the present invention, a reagent for assaying the activity of CK isozyme constituted by reagents necessary for the measurement method of the present invention as a kit or as a single item. As the reagent referred to herein, a reagent for assaying CK-MB which is used for acute myocardiac infarction may be used as a part thereof. However, the present invention is not limited thereto.

EXAMPLES

The following examples will explain the present invention concretely. However, the present invention is not limited thereto.

Example 1

Preparation Method for Polyclonal Antibody (1) Rabbit

NZW/clean (Carey) rabbits, male, weighing 1.25 to 1.35 kg/animal when they were procured, were raised in an animal raising chamber on standard pellets with free water supply.

(2) Preparation of Immunogen

Human mCK was purified from a human cardiac muscle tissue and a human gastric tissue according to the methods described in R. Roberts et al., *J. B. C.*, Vol. 255, pp. 2870–2877 (1980) and A. M. Grace et al., *J. B. C.*, Vol.258, pp.15346–15354 (1983). From about 300 g of a human cardiac muscle was obtained purified smCK. Similarly about 150 g of a human stomach was obtained purified umCK. These were cryopreserved until they were used.

(3) Immunization method

Antigens smCK and umCK prepared in (2) above were each adjusted to 100 μg/ml with RiBi Adjuvant (MPL+ TDM) and vigorously mixed to prepare homogeneous suspensions. Then, the suspensions were each administered to three rabbits at the groins each in 200 μl and at two sites on the back each in 50 μl. Moreover, the above antigen adjusted in the same manner as above was repeated administered every four weeks in total four times.

(4) Measurement of antibody titer

Upon measurement of antibody titers, a small amount of whole blood was periodically collected from the auricular veins of rabbits and sera were separated therefrom. Then, the sera were treated at 55° C. for 60 minutes to inactivate the activity of CK in the leporine sera and cryopreserved until use. From the onset of immunization, antibody titers against smcK and umCK were examined by an mCK enzymatic activity inhibitory antibody method.

More specifically, the serum from each rabbit was diluted. 100-folds with PBS to prepare 50 μl of an antibody solution. This was collected in wells of a 96-well microtiter plate, to which was added 50 μl of an mCK enzyme solution (PBS buffer containing 0.2 U/ml of smCK or umCK), and the mixture was left to stand at room temperature for 10 minutes. Thereafter, 100 μl of a CK coloring reagent [100 mM imidazole, 2 mM EDTA, 10 mM magnesium acetate, 2 mM adenosine-5'-diphosphate (ADP), 5 mM adenosine-5'-monophosphate (AMP), 40 μM P1, P5-di (adenosine-5')-pentaphosphate (AP5A), 30mM 1-thioglycerol, 20 mM D-glucose, 2 mM NADP, 3 U/ml hexokinase, 2 U/ml glucose-6-phosphate dehydrogenase, 30 mM creatine phosphate, 1 mg/ml Nitro Blue Tetrazolium, 3 U/ml diaphorase, pH 6.6] was added and the mixture was allowed to react at 37° C. for 10 minutes.

Subsequently, each of the above wells was added 50 μl of 0.2 N hydrochloric acid to stop the reaction and absorbance at 570nm was measured using pure water as a control. Furthermore, where the obtained absorbance suggested inhibition of the enzymatic activity of mCK, the change in absorbance is small due to suppressed substrate reaction and the existence of an enzymatic activity inhibiting specific antibody could be identified. To note, as a negative control of antibody, the one which contains only PBS was used and as a blind control for sample, PBS was used instead of the mCK enzyme solution.

(5) Study of reaction specificity

Enzyme solutions containing optimal concentrations of human CK-MB and human CK-MM, respectively, were prepared and the anti-human smCK inhibitory antibody and umCK inhibitory antibody obtained as described above were examined for their inhibition of the enzymatic activity against the respective enzymes in the same manner as described above.

Example 2

The following reagents were prepared as CK activity assaying reagents.

Enzyme reagent: 140 mM imidazole, 2.8 nM EDTA, 14 mM magnesium acetate, 2.8 mM adenosine-5'-diphosphate (ADP), 7 mM adenosine-5'-monophosphate (AMP), 14 μM P1,P5-di(adenosine-5') pentaphosphate (AP5A), 42 mM 1-thioglycerol, 28 mM D-glucose, 2 mMNADP, 4.2 U/ml hexokinase, 2.1 U/ml glucose-6-phosphate dehydrogenase, pH 6.6 Substrate solution: 150 mM disodium creatine phosphate Fractionation reagent: 1 U/ml anti-human smCK inhibitory antibody (rabbit) or umCK inhibitory antibody (rabbit) was added to the enzyme reagent to prepare a fractionation liquid.

To 20 μl each of 5-level dilutions of purified human CK (physiological saline containing 0.1% BSA) was added 250 μl of the enzyme reagent and the mixture was kept at a constant temperature of 37° C. Thereafter, it was measured of a change in absorbance at a wavelength of 340 nm (A). Furthermore, 2 to 3 minutes after the addition of 100 μl of the substrate solution, a change in absorbance was also measured (B) The activity of CK was calculated according to the following equation (mathematical formula 1).

$$CK \text{ Activity (U/L)} = \frac{(370 \times B - 270 \times A) \times 1000}{6.3 \times 20} \quad \text{Mathematical formula 1}$$

Next, similar operation was made using the fractionation reagent instead of the enzyme reagent to measure a change in absorbance and thus the activity of CK. The activity of CK was calculated by the above equation (mathematical formula 1). The results obtained are shown in Tables 2 to 4. The antibody inhibited human mCK but not inhibited CK-M subunit and CK-B subunit.

TABLE 2

Influence of an inhibitory antibody on the activity of CK-MM (U/L).

| Dilution | 0 | 1/5 | 2/5 | 3/5 | 4/5 | 5/5 |
|---|---|---|---|---|---|---|
| Anti-mCK Antibody absent | 0 | 752 | 1496 | 2262 | 3010 | 3748 |
| Anti-smCK Antibody present | 0 | 747 | 1496 | 2250 | 2998 | 3740 |
| Anti-umCK antibody present | 0 | 750 | 1490 | 2258 | 3002 | 3745 |

TABLE 3

Influence of an inhibitory antibody on the activity of CK-BB (U/L).

| Dilution | 0 | 1/5 | 2/5 | 3/5 | 4/5 | 5/5 |
|---|---|---|---|---|---|---|
| Anti-mCK Antibody absent | 1 | 28 | 57 | 85 | 115 | 143 |
| Anti-smCK Antibody present | 0 | 30 | 58 | 87 | 114 | 140 |
| Anti-umCK Antibody present | 0 | 30 | 61 | 87 | 116 | 143 |

TABLE 4

Influence of an inhibitory antibody on the activity of CK-MM (U/L) and the activity of umCK (U/L)

| Dilution | 0 | 1/5 | 2/5 | 3/5 | 4/5 | 5/5 |
|---|---|---|---|---|---|---|
| smCK Activity | | | | | | |
| Anti-mCK Antibody absent | 1 | 31 | 64 | 95 | 124 | 157 |
| Anti-smCK Antibody present | 0 | 1 | 0 | 1 | 1 | 1 |
| Anti-umCK antibody present | 0 | 2 | 3 | 3 | 4 | 4 |
| UmCK Activity | | | | | | |
| Anti-mCK Antibody absent | 0 | 25 | 51 | 75 | 101 | 128 |
| Anti-smCK Antibody present | 0 | 1 | 1 | 2 | 4 | 3 |
| Anti-umCK antibody present | 1 | 0 | 1 | 2 | 1 | 2 |

Inhibition cross-reactivity was observed regardless of whether the antibody was prepared using smCK or umCK. Therefore, the following examples were practiced using an anti-human smCK inhibitory antibody. In the following examples, the antibody expressed anti-human mCK inhibitory antibody is anti-human smCK inhibitory antibody having the inhibition cross-reactivity.

Example 3

To 100 μl each of a sample from a healthy human and human mCK-positive sample was added 10 μl each of physiological saline, anti-human CK-M inhibitory antibody (goat), anti-human mCK inhibitory antibody (rabbit), or a mixture of the two inhibitory antibodies and electrophoresis was performed for 40 minutes using Pol-E-Film System™ (Agarose electrophoresis). After the electrophoresis, the CK coloring reagent prepared in Example 1 was infiltrated into the electrophoreses gel, which was incubated at 37° C. for 30 minutes. After stopping the reaction with an aqueous 5% acetic acid solution and washing with purified water, the gel was dried and copied. The results are shown in FIG. 1. The results suggest the anti-human CK-M inhibitory antibody alone does not inhibit mCK so that mCK will be measured as CK-MB and that use of the anti-human CK-M inhibitory antibody and anti-human mCK inhibitory antibody in combination enables specific measurement of CK-MB.

Example 4

A formulation (control method) was prepared by adding 1.0 U/ml of an anti-human CK-M inhibitory antibody (goat) to the enzyme reagent of Example 2 and another formulation (the present invention) was prepared by adding 1.0 U/ml of an anti-human CK-M inhibitory antibody (goat) and further 1 U/ml of an anti-human mCK inhibitory antibody (rabbit) to the enzyme reagent of Example 2. Nineteen (19) samples showing a CK activity of 300 U/L or less and 26 samples from patients suffering liver disease, showing a GPT activity of 80 U/L or more were measured of the activity of CK-MB by the operation method of Example 2 and comparison was made. The activity of CK-MB was calculated by the following equation (mathematical formula 2).

$$CK - MB \text{ Activity (U/L)} = \frac{(370 \times B - 270 \times A) \times 1000 \times 2^*}{6.3 \times 20} \quad \text{Mathematical formula 2}$$

$2^*$: Factor converting $CK - B$ activity into $CK - MB$ activity.

The results are shown in Tables 5 and 6. From the results shown in Table 5, it revealed that the average value of CK-MB activity was 13 U/L in the control method in contrast to 7 U/L in the present invention, which was about the half of the former. Conventionally, the cut-off value of CK-MB activity has been said to be about 25 U/L. However, in the present invention, the activity of mCK which reacts non-specifically can be inhibited so that the cut-off value can be set to about 10 U/L.

As shown in Table 6, among the samples from patients suffering liver disease, 7 samples showed an activity of 25 U/L or more in the control method though they were not samples from patients suffering acute myocardiac infarction. However, in the present invention, all the samples showed an activity of 10 U/L or less.

From the above results, it is expected that due to a decrease in the cut-off value of CK-MB activity, the present invention will provide a higher sensitivity and specificity as an early marker for acute myocardiac infarction than conventional measurment method.

Example 5

Anti-human mCK inhibitory antibody may be added to the enzyme reagent or to the substrate solution. Furthermore, it is possible to prepare an anti-human mCK inhibitory antibody solution as a separate reagent from the substrate solution and the enzyme reagent, perform conventional measurement of the activity of CK-MB using the enzyme reagent containing an anti-CK-M inhibitory antibody and the enzyme, add the anti-human mCK inhibitory antibody solution, and then measure the activity of mCK, followed by subtracting the activity of mCK from the activity of CK-MB. The advantage in this case is that the activity of mCK besides the activity of CK-MB can be obtained. Hereinafter, an example thereof will be described.

Blood was periodically collected from patients whose prognosis was good and those whose prognosis was bad and were dead after the onset of acute myocardiac infarction. The samples were used for simultaneous measurement of the activity of CK-MB and the activity of mCK.

To 20 μl of each sample was added 250 μl of a reagent obtained by adding the anti-human CK-M inhibitory antibody to the enzyme reagent of Example 2 and the mixture was kept at a constant temperature of 37° C. Thereafter, the mixture was measured of a change in absorbance at a wavelength of 340 nm (A). Next, 100 μl of the substrate solution was added and after 2 to 3 minutes, a change in absorbance was measured (B). Then, 50 μl of the anti-human mCK inhibitory antibody (100 mM imidazole buffer containing 5.7 U/ml, pH 6.6) and after 2 to 3 minutes, a change in absorbance was measured (C). The activity of CK-MB and the activity of mCK were calculated by the following equation (mathematical formula 3). They were compared with the activity of CK-MB obtained by the control method. The results are shown in Tables 7 and 8 and FIGS. 2 and 3.

From the results, it can be seen that in cases where the prognosis was good, no difference was observed between the control method and the assay method of the present invention until the peak was reached after the onset of acute myocardiac infarction while in the recovery phase where the activity of CK-MB decreased, the assay method of the present invention gives lower values, indicating faster recovery.

It is believed that this is because in an early phase, the CK-MB originated from cytoplasm exudes and thereafter exudation of the mCK originated from mitochondria occurs along with the necrosis of cells. Thus, it is understood that usefulness of the method of the present invention in observing the course of prognosis is increased. In cases where the prognosis was good, the activity of mCK changes to a lower level while in cases where the prognosis is bad, the activity of mCK changes to a higher level.

Since enzymes in mitochondria will not exude in blood until the necrosis of cells occurs, currently mGOT (mitochondria glutamic acid-oxaloacetic acid transaminase) activity is measured. However, use of the present invention makes it possible to accurately measure the activity of CK-MB and at the same time obtain information on the severity of acute myocardiac infarction and on the prognosis by analogy with the degree of necrosis of cells.

$$CK-MB \text{ Activity (U/l)} = \frac{(420 \times C - 270 \times A) \times 1{,}000 \times 2^*}{6.3 \times 20} \quad \text{Mathematical formula 3}$$

$2^*$: Factor converting $CK-B$ activity into $CK-MB$ activity.

$$mCK \text{ Activity (U/L)} = \frac{(370 \times B - 420 \times C) \times 1{,}000}{6.3 \times 20}$$

TABLE 5

Results of measurement of CK-MB activity of samples having a CK activity of 300 U/L or less

| Sample No. | Control method | Invention |
|---|---|---|
| 1 | 8.9 | 3.7 |
| 2 | 10.9 | 5.1 |
| 3 | 10.0 | 5.0 |
| 4 | 16.9 | 8.7 |
| 5 | 8.4 | 2.9 |
| 6 | 22.5 | 10.0 |
| 7 | 13.8 | 7.3 |
| 8 | 17.0 | 8.5 |
| 9 | 10.8 | 5.8 |
| 10 | 18.3 | 9.0 |
| 11 | 9.9 | 5.4 |
| 12 | 6.7 | 3.2 |
| 13 | 19.1 | 9.9 |
| 14 | 9.6 | 4.8 |
| 15 | 19.4 | 8.9 |
| 16 | 15.2 | 9.0 |
| 17 | 8.6 | 3.4 |
| 18 | 9.0 | 6.0 |
| 19 | 17.2 | 9.1 |
| Average | 13.3 | 6.7 |
| SD | 4.7 | 2.4 |
| Average + 2SD | 22.7 | 11.5 |
| Average − 2SD | 3.9 | 1.9 |

TABLE 6

Results of measurement of CK-MB activity of samples having a GPT activity of 80 U/L or more

| Sample No. | Control method | Invention |
|---|---|---|
| 1 | 11.4 | 6.9 |
| 2 | 5.1 | 2.0 |
| 3 | 8.0 | 4.8 |
| 4 | 5.8 | 2.6 |
| 5 | 6.8 | 3.2 |
| 6 | 18.2 | 7.7 |
| 7 | 11.4 | 5.3 |
| 8 | 35.7 | 9.0 |
| 9 | 4.4 | 2.0 |
| 10 | 19.7 | 8.8 |
| 11 | 10.4 | 4.9 |
| 12 | 13.3 | 5.2 |
| 13 | 27.9 | 9.3 |
| 14 | 11.5 | 6.7 |
| 15 | 8.5 | 4.0 |
| 16 | 25.1 | 8.8 |
| 17 | 10.2 | 4.9 |
| 18 | 6.9 | 3.0 |
| 19 | 10.5 | 4.5 |
| 20 | 42.8 | 7.5 |
| 21 | 8.7 | 4.5 |
| 22 | 30.6 | 5.7 |
| 23 | 34.6 | 8.9 |
| 24 | 6.7 | 2.6 |
| 25 | 22.8 | 8.2 |
| 26 | 47.9 | 9.4 |
| Average | 17.1 | 5.8 |
| SD | 12.5 | 2.5 |
| Average + 2SD | 42.1 | 10.8 |
| Average − 2SD | −7.9 | 0.8 |

TABLE 7

Cases with good prognosis

| Time after Onset | Control method (CK-MB) + 2 × mCK | Invention CK-MB | mCK |
|---|---|---|---|
| 4 | 42 | 31 | 4 |
| 6 | 90 | 80 | 4 |
| 8 | 190 | 175 | 6 |
| 10 | 325 | 310 | 5 |
| 12 | 486 | 475 | 6 |
| 14 | 480 | 460 | 8 |
| 18 | 380 | 338 | 18 |
| 21 | 313 | 276 | 20 |
| 24 | 235 | 191 | 22 |
| 33 | 165 | 105 | 28 |
| 45 | 62 | 12 | 25 |
| 63 | 40 | 11 | 14 |
| 75 | 23 | 10 | 7 |
| 99 | 15 | 5 | 5 |

TABLE 8

Cases with bad prognosis

| Time after Onset | Control method (CK-MB) + 2 × mCK | Invention CK-MB | mCK |
|---|---|---|---|
| 2 | 32 | 22 | 4 |
| 4 | 64 | 51 | 4 |
| 7 | 201 | 191 | 4 |
| 9 | 385 | 371 | 6 |
| 13 | 532 | 515 | 10 |

TABLE 8-continued

Cases with bad prognosis

| Time after Onset | Control method (CK-MB) + 2 × mCK | Invention | |
|---|---|---|---|
| | | CK-MB | mCK |
| 16 | 610 | 570 | 18 |
| 20 | 630 | 536 | 45 |
| 24 | 598 | 385 | 104 |
| 28 | 578 | 266 | 154 |
| 34 | 460 | 145 | 155 |
| 42 | 390 | 70 | 158 |

INDUSTRIAL APPLICABILITY

Currently, the specificity of measurement of the activity of CK-MB is increased by addition of an antibody that specifically inhibits the activity of CK-MM to the reagent system. However, the activity of mCK is also measured so that the activity of CK-MB specific to the one originated from cardiac muscle is not always measured. In the present invention, by using an anti-human mCK inhibitory antibody to specifically inhibit the activity of mCK which has not been distinguished conventionally, it is possible to make an accurate measurement of the activity of CK-MB. The assay method of the present invention uses an anti-human mCK inhibitory antibody and specifically inhibit the activity of mCK in the serum of patients suffering acute myocardiac infarction, thereby measuring true CK-MB activity. This makes it possible to grasp severity of acute myocardiac infarction and pathological state more credibly. The present invention enables not only early diagnosis but also monitoring of its therapy of acute myocardiac infarction so that it has a great importance in clinical tests.

What is claimed is:

1. In a method for measuring the activity of creatine kinase MB isozyme in a fluid sample of a patient wherein an inhibition method is used to measure the enzymatic activity of creatine kinase (CK) isozymes, said inhibition method comprising contacting with an inhibitory antibody to human CK-M subunit to eliminate the CK-M subunit therein determining the activity of the remaining CK-MB subunit, the improvement comprising contacting the sample with an inhibitory antibody that binds to CK-M subunit (CK-M) to eliminate the enzymatic activity of the CK-M subunit and an inhibitory antibody that binds mitochondrial CK (m-CK) is used to eliminate the enzymatic activity of m-CK, and thereafter determine the enzymatic activity of remaining creatine kinase isozymes as the CK-MB isozyme in the sample.

2. The method of claim 1, wherein the inhibition of the enzymatic activity of CK-M and the inhibition of the enzymatic activity of m-CK are carried out simultaneously in one step.

3. The method of claim 1 wherein the inhibition of the enzymatic activity of CK-M and the inhibition of the enzymatic activity of m-CK are carried out in separate steps.

4. The process of claim 1 in which the method is carried out using a reagent kit containing said one or more reagents.

5. The process of claim 1 wherein each inhibitory antibody is an anti-human antibody.

6. The method of claim 1 wherein one reagent contains both the inhibitory antibody that binds to the CK-M subunit and the inhibitory antibody that binds to m-CK.

7. The method of claim 1 wherein one reagent contains the inhibitory antibody that binds to the CK-M subunit and a second reagent contains the antibody that binds to m-CK.

* * * * *